United States Patent [19]

Stashenko

[11] Patent Number: 5,328,829
[45] Date of Patent: Jul. 12, 1994

[54] METHOD OF DETERMINING SITES OF ACTIVE PERIODONTAL DISEASE

[75] Inventor: Philip Stashenko, Norfolk, Mass.

[73] Assignee: Forsyth Dental Infirmary for Children, Boston, Mass.

[21] Appl. No.: 548,093

[22] Filed: Jul. 5, 1990

[51] Int. Cl.$^5$ .................... G01N 33/53; G01N 33/535
[52] U.S. Cl. ..................... 435/7.9; 435/7.92; 435/960; 436/63; 436/811; 436/815
[58] Field of Search ............ 435/7.9, 7.92, 69.5, 435/69.52, 960; 436/63, 811, 815

[56] References Cited

U.S. PATENT DOCUMENTS 4,772,685 9/1988 Schmidt et al. ............... 530/326

OTHER PUBLICATIONS

Kamagata, Y., et al., Index Medicus, the abstract No. 91231761, (Sep. 1989).
Masada, M. P., et al., Biological Abstracts, vol. 90, No.4, the abstract No. 37143 (1990).
Honig, J., et al., Biological Abstracts, vol. 89, No.6, the abstract No. 56654 (1990).
Goodson, J. M., et al, J. Clin. Peridont., vol. 9, pp. 472–481, 1982.
Jandinski, J., et al., J. Dent. Res, vol. 67, (Spec. Issue Mar. 1988) p. 401, abstract No. 2307.
Kenney, J., et al., J. Immunol., vol. 138, No. 12, Jun. 15, 1987, pp. 4236–4242.

Primary Examiner—Toni R. Scheiner
Attorney, Agent, or Firm—Richard P. Crowley

[57] ABSTRACT

The present invention comprises a method for the determination of periodontal disease active sites within the human oral cavity by a measurement of the level of interleukin 1 beta (IL-1b) in oral tissues and gingival crevicular fluid at a particular site.

9 Claims, 2 Drawing Sheets

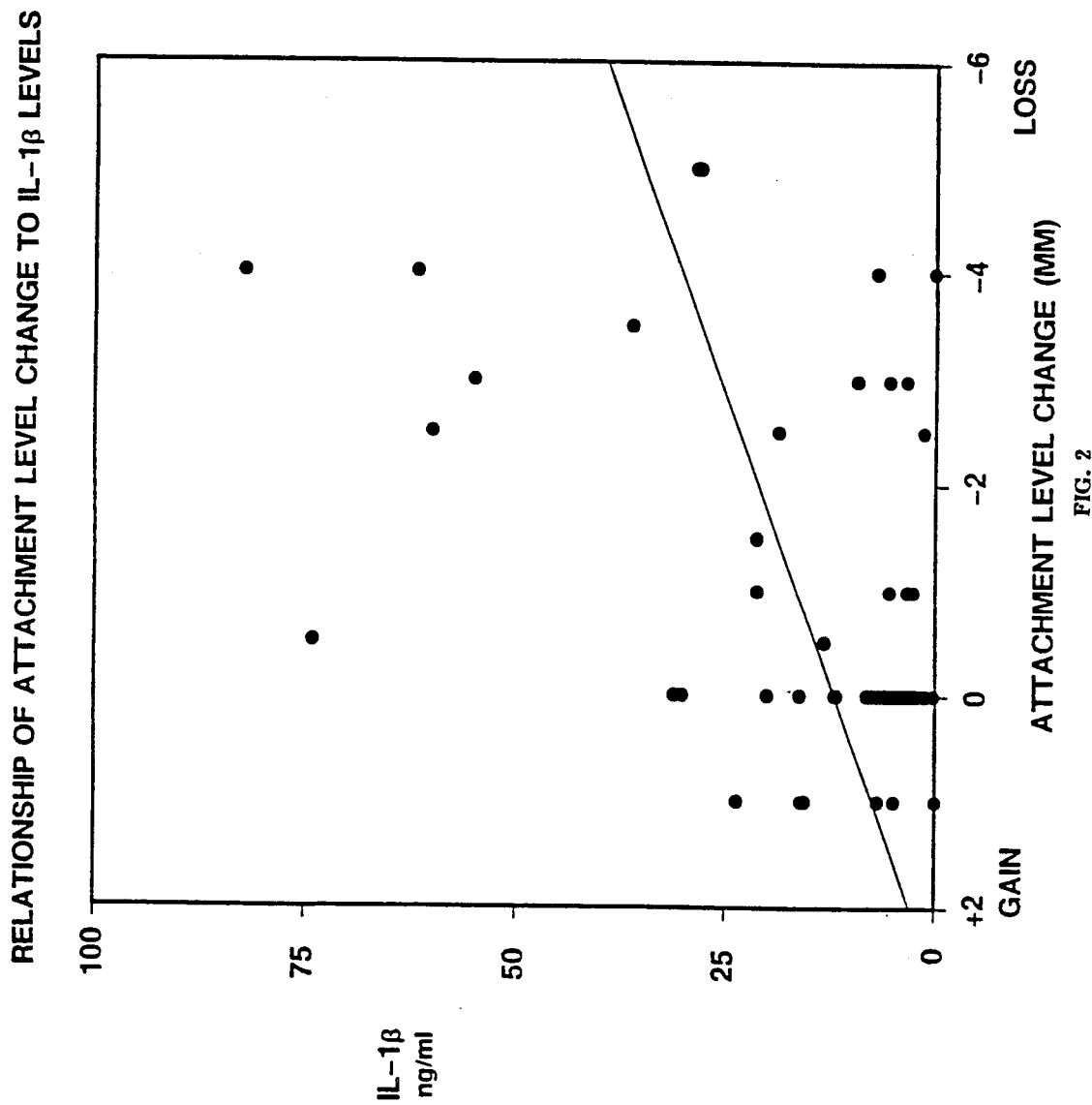

METHOD OF DETERMINING SITES OF ACTIVE PERIODONTAL DISEASE

REFERENCE TO GOVERNMENT SUPPORT

This invention was made with government support and Grant P50DE04881 awarded by the National Institute of Dental Research. The government has certain rights in the invention.

BACKGROUND OF THE INVENTION

Interleukin 1 beta (IL-1b) is a highly potent bone resorptive cytokine which is responsible for most of the activity formerly referred to as osteoclast activating factor, or 'OAF' (Dewhirst et al. 1985). IL-1b is produced in large amounts by macrophage-monocytes in response to a variety of stimuli, including bacterial components such as LPS (Burchett et al. 1988). IL-1b exerts other biological activities consistent with its potential role as a local mediator of tissue destruction in human periodontitis. These include inhibition of bone formation (Stashenko et al. 1987, Nguyen et al. 1990), stimulation of prostaglandin and thromboxane synthesis (Tatakis 1988), stimulation of collagenase and protease production (Mizel et al. 1981, Saklatvala et al. 1985), potentiation of neutrophil degranulation and superoxide production (Dinarello 1989), enhancement of endothelial cell-leukocyte adhesion (Bevilacqua et al. 1987), and stimulation of fibroblast and keratinocyte proliferation (Schmidt et al. 1982). IL-1-like activity is present in elevated amounts in crevicular fluid adjacent to sites of gingival inflammation (Charon et al. 1982). Recently IL-1b-containing cells were shown to be present in greater numbers in diseased as compared to clinically-healthy periodontal tissues (Jandinski et al. 1990).

Substantial evidence indicates that periodontal destruction is not continuous, but rather occurs episodically in bursts of disease activity (Goodson et al. 1982). At any given point in time the majority of sites with periodontal disease involvement are in fact quiescent. An important consequence of this finding is that putative host or bacterial indicators of periodontal disease must be evaluated in the temporal context of these relatively infrequent events (Caton 1990). It is therefore desirable to provide an effective method of determining periodontal disease active sites in the oral cavity of a patient.

SUMMARY OF THE INVENTION

The invention relates to a method for the determination and detection of active periodontal disease sites by a measurement of the level of (IL-1b).

It has been discovered that IL-1b levels in tissues obtained from the site of active periodontal destruction has been found to be indicative of active periodontal disease sites. An elevated level of the IL-1b in sites of disease activity compared to previous disease in inactive and in healthy sites has shown that an elevated level of IL-1b indicates an active periodontal disease site. Studies have indicated that IL-1b levels of greater than about 25 nanograms per millimeter in gingival tissues correlated with periodontal disease activity and that therefore the level of IL-1b serves as a useful diagnostic marker of these periodontal destructive events. Such a diagnostic marker of periodontal disease activity is useful to the dental practitioner in deciding whether or not to treat a patient using periodontal therapy, such as surgery, antibiotics or both, and also in monitoring patient response and the success or failure of the therapy employed.

The level of IL-1b may be determined in tissues obtained from the sites in the oral cavity from which a determination needs to be made. However, IL-1b may be measured non-invasively, and preferably, by determining the amount and concentration in gingival crevicular fluid (GCF). GCF is the fluid present in the periodontal pocket adjacent the teeth. GCF represents a transudate of serum which also contains substances produced locally in the periodontal tissues, including IL-1b. IL-1b levels in GCF appear to reflect adjacent tissue levels, and therefore, the level of the IL-1b in the determination of a periodontal disease active site may be determined through the determination of the IL-1b in the tissue, or more preferably, by a simple, rapid, in-office diagnostic, preferably a color test, by measuring the IL-1b in the GCF.

Studies have been carried out using a commercially available IL-1b ELISA (enzyme-linked immunoassay) test kit purchased from Cistron Biotechnology of Pinebrook, N.J., which test is not appropriate for rapid chairside testing in its present form due to its complexity. However, an antibody-based detection kit which was fast and simple and gives a readily interpretable output, e.g. color development, for the determination of IL-1b and the detection of periodontal disease would be most useful.

Levels of IL-1b were determined in tissue obtained from (1) diseased, active (n=14) (2) diseased, inactive (n=32), and (3) healthy sites (n=4) from twelve patients with destructive adult periodontitis. All patients had experienced attachment loss of $\geq 3.0$ mm at one or more sites during the preceding two-month period, as determined by sequential probing and the tolerance method. At surgery, IL-1b was extracted from homogenates of tissue, biopsies and levels were quantitated by ELISA (kit from Cistron Biotechnology, Inc.). IL-1b was found to be present in most patient tissue samples, with levels ranging from 0–82 ng/ml by ELISA. Disease active sites had higher IL-1b levels ($p<0.05$) than inactive or healthy sites. Of interest, diseased inactive sites which had experienced amounts of attachment loss (0.5–2.5 mm) not considered significant by our stringent criteria, had IL-1b levels significantly higher than diseased sites showing no change or attachment gain. For all sites, IL-1b levels $>25$ ng/ml significantly correlated with disease activity ($p<0.01$). IL-1b levels were also positively related to attachment level, pocket depth, but were negatively related to the presence of supragingival plaque or redness and unrelated to bleeding on probing or suppuration, indicating a dissociation between the presence of inflammation and IL-1b levels.

MATERIALS AND METHODS

Subject population

The subject population consisted of 12 adult periodontitis patients (mean age: 47.0 years, range: 28–65) who had experienced significant attachment loss in at least one site during the preceding 2 month period. The subjects were monitored longitudinally as previously described (Haffajee et al. 1983a). All subjects were systemically healthy and had not received periodontal therapy or antibiotics during the previous 6 months. Replicate attachment level and pocket depth measurements were taken at 6 sites per tooth every 2 months. Dichotomous measurements of supragingival plaque, redness, suppuration, and bleeding on probing were also made at 6 sites per tooth once every 2 months. Disease activity was defined by the tolerance method (Haffajee et al. 1983a). The active sites exhibited attachment loss ≧2.5 mm during the preceding 2 month period. Subjects were recalled within 2 weeks of the detection of disease activity for surgical treatment.

Sample collection and extract preparation

Quadrant surgery was carried out using a modified Widman flap procedure. Tissue samples from the active site and adjacent sites which manifested past evidence of disease were collected and processed individually. Tissues were rinsed in RPMI 1640 medium containing gentamycin (50 μg/ml), freed of clots and debris, blotted, weighed, and immediately frozen and stored in liquid $N_2$.

For extract preparation, tissues were finely minced with a scalpel, and the fragments were incubated at 100 mg tissue/ml of a digestion mixture consisting of 500 U/ml collagenase (Sigma, Type VII), 100 μg/ml bovine serum albumin, 100 μg/ml Zwittergent-12 (Calbiochem), 50 μg/ml gentamycin, and 10 mM Hepes buffer in RPMI 1640. After 60-90 min at 37° C. with continual agitation, the digestate was placed on ice and was subjected to 20-30 sec sonication to further disaggregate tissues. This procedure caused complete tissue dispersion and cell lysis, and liberated IL-1$\beta$ from both inter- and intracellular compartments. Debris was removed by centrifugation and supernatants were immediately tested for IL-1$\beta$ content using an ELISA assay (Cistron Biotechnology, Pinebrook N.J.).

IL-1$\beta$ assay

Assays were carried out in accordance with manufacturer's instructions, with modifications. In brief, 100 μl of tissue extract were assayed in duplicate at 2 dilutions, usually neat or ½, and 1/10 as amounts permitted. Following overnight incubation with monoclonal anti-IL-1$\beta$-coated assay wells at 4° C., plates were washed ×3, and subsequently were reacted with 100 μl rabbit anti-IL-1$\beta$ antiserum for 2 hours at 37° C. Plates were washed ×3, and were then incubated with 100 μl goat anti-rabbit IgG-horse radish peroxidase conjugate at room temperature for 30 min. Following a final series of washes, the assay was developed by the addition of 100 μl of o-phenylenediamine and hydrogen peroxide. The reaction was terminated after 15 min by the addition of 50 μl 4N sulfuric acid, and the color was quantitated at 490 nm using a Hewlett-Packard plate reader. The amount of IL-1$\beta$ in tissue samples was determined by reference to a standard curve (0-1000 pg/ml) constructed with each assay. The curve was reproducibly linear in the range of 50-1000 pg/ml.

Recombinant human IL-1$\beta$, interleukin-1$\alpha$ (IL-1$\alpha$), and tumor necrosis factor $\alpha$ (TNF$\alpha$), used to confirm the specificity of the ELISA, were generously provided by the following investigators: IL-1$\beta$, Dr. R. Newton, E. I. Dupont, Glenolden, Pa; IL-1$\alpha$, Dr. K. Jacobs, Genetics Institute, Cambridge, Mass.; TNF$\alpha$, Dr. L. Lin, Cetus Corp., Emeryville, Calif.

Statistical analysis

The IL-1$\beta$ content of tissue samples was expressed as ng IL-1$\beta$/ml, assuming the wet weight of tissue to be 1.0 g/ml. Differences in IL-1$\beta$ levels were sought using the Mann Whitney test (2 groups) and the Kruskal-Wallis test (more than 2 groups) with appropriate correction for multiple comparisons.

RESULTS

Validation experiments

Several preliminary experiments were carried out to validate the methodology used in these studies. The specificity of the assay for IL-1$\beta$ was first assessed. As shown in Table 1, only IL-1$\beta$ produced a positive reaction in the ELISA at 100 pg/ml, whereas 2 other human bone resorptive monokines, recombinant interleukin 1$\alpha$ (IL-1$\alpha$) and tumor necrosis factor $\alpha$ (TNF$\alpha$), were completely negative even at 10,000 or 100,000 pg/ml. The possible effect of tissue proteins, including tissue proteases, on IL-1$\beta$ content was explored in an add-back experiment. Extracts were made from 2 tissue samples from diseased but inactive sites. These were tested for IL-1$\beta$ content alone, and in the presence of a known amount of added IL-1$\beta$ (500 pg/ml). As Table 1 demonstrates, the total amount of IL-1$\beta$ detected under these conditions was closely similar to the initial plus added amount. This finding indicates that tissue extract proteins did not interfere with IL-1$\beta$ measurement, nor did there appear to be significant degradation of IL-1$\beta$. Finally, the incubation of known amounts of IL-1$\beta$ with collagenase, used to aid tissue disaggregation, failed to affect the amount of IL-1$\beta$ detected, indicating a lack of protease activity in the collagenase preparation (data not shown).

Clinical parameters of sites

Periodontal tissue samples of sufficient size to permit analysis were obtained from a total of 50 sites in 12 subjects with adult forms of periodontitis. These consisted of 14 active sites, defined as sites with ≧2.5 mm attachment loss over the preceding 2 month period; 32 diseased but inactive sites, defined as sites with periodontal disease involvement, but with either small amounts of attachment loss, no loss, or even attachment gain; and 4 healthy sites. The clinical parameters of these sites are presented in Table 2. Mean pocket depth and attachment levels were significantly greater in disease active sites than in disease inactive and healthy sites, an expected association given that disease activity is defined by recent increases in attachment level ($p<0.001$). Note should be made of the so-called healthy sites. In our studies healthy sites are normally defined as sites without redness, bleeding or probing, and with attachment level and pocket depth <4 mm. However, because the patients in this study had extensive disease, completely healthy sites were rare and were often located outside the area of surgery. Moreover, many of the healthy sites sampled at surgery yielded too little tissue for analysis. Thus, tissue from only 4 healthy sites was available for analysis. These sites fulfilled the criteria for clinical health except that 2 exhibited redness.

IL-1$\beta$ levels in periodontal tissues: Relationship to attachment loss

The IL-1$\beta$ levels present in extracts of tissue samples were determined by ELISA, and the results are summarized in Table 3. Most samples, regardless of clinical status, had some detectable IL-1$\beta$, and overall, measured concentrations ranged from 0-82 ng/ml. Of interest, tissue IL-1$\beta$ was found in highest amounts in the active sites. These levels were significantly higher ($p<0.01$) than levels present in the combined diseased, but inactive sites and healthy sites. As seen in FIG. 1, a wide range of values of IL-1β were obtained for all 3 groups of sites. Nonetheless, a value of IL-1β above 25 ng/ml had a significant probability of association with active disease, as determined by Chi-Square analysis ($X2=6.76$, $p<0.01$) (Table 4).

TABLE 1

Validation studies of IL-1β measurements by ELISA

| Test Sample | Concentration (pg/ml) | Optical Density @ 490 nm** | IL-1β (pg/ml)* |
|---|---|---|---|
| IL-1β | 100 | 0.152 ± 0.004 | 100 |
|  | 1,000 | 1.360 ± 0.086 | 1,000 |
| IL-1α | 10,000 | 0.000 ± 0.001 | 0 |
|  | 100,000 | 0.002 ± 0.004 | <2 |
| TNFα | 10,000 | 0.000 ± 0.001 | 0 |
|  | 100,000 | 0.002 ± 0.004 | <2 |
| Tissue 1 |  | 0.240 ± 0.004 | 160 ± 2 |
| Tissue 1 + IL-1β | 500 | 1.120 ± 0.002 | 814 ± 1 |
| Tissue 2 |  | 0.316 ± 0.017 | 211 ± 12 |
| Tissue 2 + IL-1β | 500 | 1.048 ± 0.035 | 757 ± 27 |

*determination from IL-1β standard curve.
**mean ± S.D. of duplicate measurements.

TABLE 2

Clinical parameters of sites from adult periodontitis patients

| Site designation | n | Number of sites with: Plaque | Redness | Bleeding on probing | Suppuration | Attachment level (mm)* | Pocket depth (mm)* |
|---|---|---|---|---|---|---|---|
| Active | 14 | 7 | 10 | 9 | 1 | 8.5 ± 0.7 | 8.5 ± 0.4 |
| Diseased, Inactive | 32 | 21 | 24 | 12 | 1 | 5.4 ± 0.4 | 5.5 ± 0.4 |
| Healthy | 4 | 3 | 2 | 0 | 0 | 1.8 ± 0.3 | 2.8 ± 0.3 |

*mean ± S.E.

TABLE 3

Tissue IL-1β levels in adult periodontitis

| Site designation | n | IL-1β (ng/ml)* |
|---|---|---|
| Active | 14 | 28.4 ± 7.2 |
| Diseased, inactive | 32 | 12.6 ± 2.5 |
| 'Healthy' | 4 | 6.2 ± 4.6 |

*mean ± S.E.

Active sites are identified by relatively large changes in attachment ($\geq 2.5$ mm) to minimize false positive rates. To determine the relationship between IL-1β and smaller amounts of attachment loss, disease inactive sites were divided into 2 groups; those exhibiting attachment loss of 0.5 mm to 2.0 mm (worsening sites, n=16), and those exhibiting no change or gain in attachment level (stable sites, n=16) (Table 5). Interestingly, stable sites were similar to healthy sites in terms of IL-1β levels (mean: 7.4 ng/ml), whereas IL-1β levels at sites exhibiting some attachment loss were at an intermediate level (mean: 17.9 ng/ml). The difference in IL-1β levels in stable sites was significant when compared to active sites (Kruskal-Wallis, $p<0.02$), but not when compared to worsening sites. Levels in worsening sites and active sites were not significantly different. A scatter plot of IL-1β levels and attachment level changes is presented in FIG. 2. A significant correlation was found between these parameters when all sites, regardless of status, were analyzed ($r=0.40$, $p<0.01$).

Relationship of IL-1β levels to clinical parameters

The relationship between IL-1β levels and clinical parameters at the site is shown in Table 6. IL-1β levels were higher in sites with greater pocket depth or attachment level, again an expected result given the criteria for defining disease activity (see Table 2). Interestingly, mean levels of IL-1β were higher at sites not exhibiting plaque or redness. This finding suggests a dissociation between the production of this cytokine and marginal gingivitis. There was no significant association between the levels of IL-1β and the occurrence of bleeding on probing or suppuration at a site.

TABLE 4

Relationship between elevated levels of IL-1β and disease activity

| | | Disease activity (attachment loss $\geq 2.5$ mm) | |
|---|---|---|---|
| | | − | + |
| IL-1β levels ng/ml | $\geq 25$ | 32 | 7 |
| | $>25$ | 4 | 7 |

| Odds ratio | 8.0 | $X^2$ | 6.76 | $p<0.01$ |
|---|---|---|---|---|

TABLE 5

Relationship of tissue IL-1β levels to changes in packet depth and attachment level*

| Site designation | n | Pocket depth (mm) | Δ | Attachment level (mm) | Δ | IL-1β (ng/ml) |
|---|---|---|---|---|---|---|
| Active | 14 | 8.5 ± 0.4 | −3.5 ± 0.3 | 8.5 ± 0.7 | −3.5 ± 0.2 | 28.4 ± 7.2 |
| Worsening, diseased | 16 | 5.6 ± 0.5 | −0.7 ± 0.2 | 5.9 ± 0.6 | −0.8 ± 0.1 | 17.9 ± 4.4 |
| Stable, diseased | 16 | 5.4 ± 0.6 | +0.6 ± 0.1 | 4.9 ± 0.6 | +0.3 ± 0.1 | 7.4 ± 1.5 |

*mean ± S.E.

TABLE 6

IL-1β levels at sites with different clinical parameters

| | | N | Mean ng/ml | S.E. | p*** |
|---|---|---|---|---|---|
| Plaque | 0* | 19 | 29.4 | 5.7 | <0.001 |
|  | 1** | 31 | 8.7 | 1.7 |  |
| Redness | 0 | 14 | 28.0 | 6.8 | <0.01 |
|  | 1 | 36 | 12.1 | 2.5 |  |
| BOP | 0 | 29 | 16.6 | 3.4 | NS |
|  | 1 | 21 | 16.5 | 4.7 |  |
| Suppuration | 0 | 48 | 16.0 | 2.9 | NS |
|  | 1 | 2 | 29.2 | 0.8 |  |
| Pocket depth (mm) | <4 | 6 | 7.5 | 3.4 | <0.05 |
|  | 4–6 | 24 | 9.5 | 1.5 |  |
|  | >6 | 20 | 27.7 | 5.8 |  |
| Attachment level (mm) | <4 | 9 | 7.5 | 2.3 | <0.05 |
|  | 4–6 | 22 | 10.4 | 2.0 |  |
|  | >6 | 19 | 27.9 | 6.1 |  |

*Not detected
**Detected
***Mann Whitney U test for 2 groups; Kruskal-Wallis for 3 groups It has been found from the above tests that IL-1b is present in large quantities in diseased periodontal tissues which have experienced recent attachment loss. Sites with attachment loss ≧2.5 mm over the previous 2 months had IL-1β levels which were approximately 2.5 times higher than diseased sites without significant loss, and 4.6 times higher than healthy sites. For all sites, there was a significant correlation between the levels of IL-1β and the amount of attachment loss which had occurred during the previous 2 month period (FIG. 2). Although relatively few patients and sites have thus far been analyzed, these data suggest that a significant relationship exists between the presence of a bone resorptive cytokine and active periodontal destruction.

A wide range of IL-1β levels was found in sites in all disease categories, including the active sites (0-82 ng/ml). Although a level of 25 ng/ml was significant in predicting disease activity, only half of active sites had IL-1β at these high levels. This observation may in part be attributable to the time frame of monitoring disease activity, which was carried out at 2 month intervals (Haffajee et al. 1983a). Using this design, there is no way of distinguishing whether the actual destructive event took place early, late, or even continuously throughout the preceding 2 months. Clearly, sites in which destruction had occurred late in the observation period, more proximate to surgical treatment, would be the most appropriate samples for analysis.

The use of a relatively large (≧2.5 mm) attachment loss results in the identification of active sites with very few false positives i.e. sensitivity is sacrificed in order to achieve a high degree of specificity (Haffajee et al. 1983a). It is likely that a number of sites in the 'diseased but inactive' category were active, but failed to meet the stringent criteria for attachment level change. This is substantiated by findings of Lindhe et al. (1983), in which the number of sites identified as active increased by 3-fold and 7-fold respectively, when 2 mm or 1 mm of attachment loss was accepted as significant. This hypothesis is also consistent with the finding that diseased sites with smaller amounts of attachment loss (0.5-2.0 mm, 'worsening sites'), also contained more IL-1β than did sites which remained stable. In these experiments, 32% of all sites tested fell into the 'worsening' category. The development of more sensitive measurement techniques, especially computer-linked periodontal probes (Jeffcoat et al. 1986, Gibbs et al. 1988), may help to clarify this issue.

IL-1β levels were unrelated to bleeding on probing or suppuration, and were inversely related to supragingival plaque or redness. These findings indicate that IL-1β production does not simply reflect the presence of gingival inflammation and are furthermore consistent with the previously reported divergence between clinical signs of inflammation and disease activity (Haffajee et al. 1983b). In the latter study, plaque, redness, bleeding, and suppuration were present in only a minority of active sites. We cannot readily explain why an inverse (as opposed to no) relationship should exist between supragingival plaque or redness, and IL-1β levels. Certainly, supragingival microorganisms, which are predominantly Gram-positive (Socransky 1977, van Palenstein-Helderman 1975), may not effectively stimulate IL-1β production, in contrast to Gram-negative periodontopathogens located subgingivally which possess LPS (Hanazawa et al. 1985, Burchett 1988). In addition, certain mechanisms associated with inflammation, e.g. the synthesis of prostaglandins which can down-regulate IL-1β production (Knudsen et al. 1986), could also account for this observation.

Although other cytokines including IL-1α, TNFα, and lymphotoxin (TNFβ) also possess bone resorbing and pro-inflammatory activities (Stashenko et al. 1987, Bertolini et al. 1986), this data has focused on IL-1b in these studies. IL-1b is 15-fold more potent than IL-1α, and 500-fold more potent than TNFα and lymphotoxin in mediating bone resorption in vitro (Stashenko et al. 1987). IL-1β and TNFα-containing cells are present in elevated numbers in diseased vs clinically healthy periodontal tissues, whereas IL-1α-containing cells are less frequent (Jandinski et al. 1989, 1990). Both IL-1β and TNFα have been identified in crevicular fluid from periodontitis sites (Scorziello et al. 1990, P. Stashenko, unpublished observations) However, the mean TNFα levels reported (approximately 0.5 ng/ml) are incapable of resorbing bone, at least in vitro (Stashenko et al. 1987). In contrast IL-1β stimulates half-maximal bone resorbing activity in vitro (Stashenko et al. 1987) and in vivo (Nguyen et al. 1990) at about 1 ng/ml. It therefore seems probable that the IL-1β levels measured in tissues are within the biologically-relevant range for mediating periodontal bone destruction.

A number of other indicators of disease activity have also been proposed. These include host products such as collagenase (Kryshtalsky et al. 1986), prostaglandin $E_2$ (Offenbacher et al. 1986), and β-glucuronidase (Lamster et al. 1988). The presence of periodontopathic bacteria including B. gingivalis, B. intermedius, and A. actinomycetemcomitans, has also been shown to relate to sites exhibiting periodontal breakdown (Dzink et al. 1985, Genco et al. 1986). Given the constellation of bioactivities of IL-1β, and the finding that this cytokine is present in elevated amounts in active and worsening sites, IL-1b has diagnostic utility in identifying sites at risk for periodontal destruction.

The invention will be described for the purposes of illustration only in connection with certain embodiments; however, it is recognized that those persons skilled in the art may make various modifications, changes, additions and improvements to the certain embodiments, all falling within the spirit and scope of the invention.

BRIEF DESCRIPTION OF THE DRAWINGS

FIG. 2 is a graphical representation of the relationship of IL-1B levels to attachment level change.

FIG. 1 Relationship between IL-1β levels and clinical designation of sites. Sites were categorized as active, disease but inactive, or healthy by criteria outlined in the Materials and Methods. Diseased sites were further subdivided into stable (no change, attachment gain) or worsening (0.5-2.0 mm attachment loss). Each point represents a single site. Mean ± standard error of group. The horizontal dashed line at 25 ng/ml suggests a threshold for defining active sites.

FIG. 2 Relationship between IL-1β levels and attachment level change. Scatterplot of changes in attachment over preceding 2 month monitoring period and tissue levels of IL-1β as determined by ELISA. Each point represents a single site. The regression line is IL-1β = 12.07 − 4.52 × attachment level change; r = −0.40.

References

Figure 1:
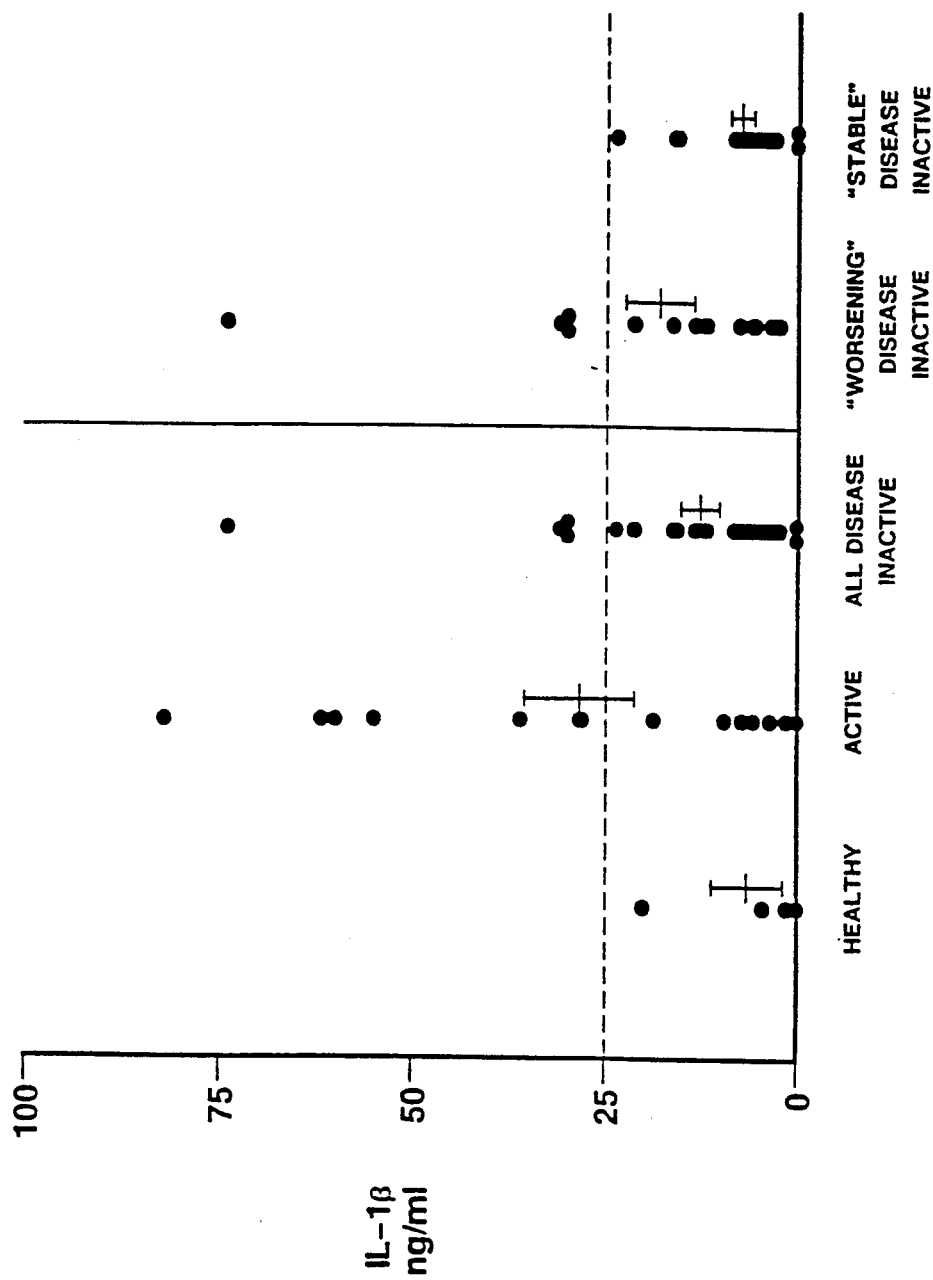
FIG. 1 is a graphical illustration of the relationship of IL-1b levels to disease status at the site.

Bertolini, D. R., Nedwin, G. E., Bringman, T. S., Smith, D. D. & Mundy, G. R. (1986) Stimulation of bone resorption and inhibition of bone formation in vitro by human tumor necrosis factors. *Nature* 31, 516-518.

Bevilacqua, M. P., Pober, J. S., Wheeler, M. E., Mendrick, D., Cotran, R. S. & Gimbrone, M. A., Jr. (1987) Interleukin-1 acts on cultured human vascular endothelium to increase the adhesion of polymorphonuclear leukocytes, monocytes, and related leukocyte cell lines. *Journal of Clinical Investigation* 76, 2003-2011.

Burchett, S. K., Weaver, W. M., Westall, J. A., Larsen, A., Kronheim, S. & Wilson, C. B. (1988) Regulation of tumor necrosis factor/cachectin and IL-1 secretion in human mononuclear phagocytes. *Journal of Immunology* 140, 3473-3481.

Caton, J. (1990) Periodontal diagnosis and diagnostic aids. In: *Proceedings of the World Workshop in Clinical Periodontics*. pp. 1-22. American Academy of Periodontology. Littleton, Mass.: PSG Publishing Company, Inc.

Charon, J. A., Luger, T. A., Mergenhagen, S. E. & Oppenheim, J. J. (1982) Increased thymocyte-activating factor in human gingival fluid during gingival inflammation. *Infectious Immunity* 38, 1190-1194.

Dewhirst, F. E., Stashenko, P., Mole, J. E. & Tsurumachi, T. (1985) Purification and partial sequence of human osteoclast-activating factor: Identity with interleukin 1β. *Journal of Immunology* 135, 2562-2568.

Dinarello, C. A. (1989) Interleukin-1 and its biologically-related cytokines. *Advances in Immunology* 44, 153-205.

Dzink, J. L., Tanner, A. C. R., Haffajee, A. D. & Socransky, S. S. (1985) Gram negative species associated with active periodontal lesions. *Journal of Clinical Periodontology* 12, 648-659.

Genco, R. J., Zambon, J. J. & Christersson, L. A. (1986) Use and interpretation of microbiological assays in periodontal diseases. *Oral Microbiology and Immunology* 1, 73-80.

Gibbs, C. H., Hirschfeld, J. W., Lee, J. G., Low, S. B., Magnusson, I., Thousand, R. R., Werneni, P. & Clark, W. B. (1988) Description and clinical evaluation of a new computerized periodontal probe—the Florida probe. *Journal of Clinical Periodontology* 15, 137-144.

Goodson, J. M., Tanner, A. C. R., Haffajee, A. D., Sornberger, G. C. & Socransky, S. S. (1982) Patterns of progression and regression of advanced periodontal disease. *Journal of Clinical Periodontology* 9, 472-481.

Haffajee, A. D., Socransky, S. S. & Goodson, J. M. (1983a) Comparison of different data analyses for detecting changes in attachment level. *Journal of Clinical Periodontology* 10, 298-310.

Haffajee, A. D., Socransky, S. S. & Goodson, J. M. (1983b) Clinical parameters as predictors of destructive periodontal disease activity. *Journal of Clinical Periodontology* 10, 257-265.

Hanazawa, S., Nakada, K., Ohmori, Y., Myoshi, T., Amano, S. & Kitano, S. (1985) Functional role of interleukin-1 in periodontal disease: induction of interleukin-1 production by *Bacteroides gingivalis* lipopolysaccharides in peritoneal macrophages from C3H/HeN and C3H/HeJ mice. *Infection and Immunity* 50, 262-270.

Jandinski, J. J., Rynar, J. E., Steinle, M., Leung, C. E., Deasey, M. J. & Stashenko, P. (1989) Localization of Interleukin 1α and tumor necrosis factor a in human gingiva. *Journal of Dental Research* 68, (Special Issue), Abstract #526.

Jandinski, J. J., Stashenko, P., Feder, L. S., Leung, C. C., Rynar, J. E. & Deasy, M. J. (1990) Localization of interleukin-1 beta in human periodontal tissue. *Journal of Periodontology*, in press.

Jeffcoat, M. K., Jeffcoat, R. L., Jens, S. C. & Captain, K. (1986) A new periodontal probe with automated cemento-enamel junction detection. *Journal of Clinical Periodontology* 13, 276-280.

Knudsen, P. J., Dinarell, D. A. & Strom, T. B. (1986) Prostaglandins posttranscriptionally inhibit monocyte expression of interleukin 1 activity by increasing intracellular cyclic adenosine monophosphate. *Journal of Immunology* 137, 3189-3194.

Kryshtalsky, E., Sodek, J. & Ferrier, J. M. (1986) Correlation of collagenolytic enzymes and inhibitors in gingival crevicular fluid with clinical and microscopic changes in experimental periodontitis in the dog. *Archives of Oral Biology* 31, 21-31.

Lamster, I. B., Oshrain, R. L., Harper, D. S., Celenti, R. S., Hovliaras, C. A. & Gordon, J. M. (1988) Enzyme activity in crevicular fluid for detection and prediction of clinical attachment loss in patients with chronic adult periodontitis. *Journal of Periodontology* 59, 516-523.

Lindhe, J., Haffajee, A. D. & Socransky, S. S. (1983) Progression of periodontal disease in adult subjects in the absence of periodontal therapy. *Journal of Clinical Periodontology* 10, 433-442.

Mizel, S. B., Dayer, J. M., Krane, S. M. & Mergenhagen, S. E. (1981) Stimulation of rheumatoid synovial cell collagenase and prostaglandin production by partially purified lymphocyte activating factor (interleukin 1). *Proceedings of the National Academy of Sciences USA* 78, 2474-2477.

Nguyen, L., Dewhirst, F. E., Hauschka, P. V. & Stashenko, P. (1990) Interleukin 1β stimulates bone resorption and inhibits bone formation in vivo. *Journal of Bone and Mineral Research*, submitted.

Offenbacher, S., Odle, B. M. & Van Dyke, T. E. (1986) The use of crevicular fluid prostaglandin E2 levels as a predictor of periodontal attachment loss. *Journal of Periodontal Research* 21, 101-112.

Saklatvala, J., Sarsfield, S. J. & Townsend, Y. (1985) Pig interleukin-1. Purification of two immunologically different leukocyte proteins that cause cartilage resorption, lymphocyte activation, and fever. *Journal of Experimental Medicine* 162, 1208-1222.

Schmidt, J. A., Mizel, S. B., Cohen, D. & Green, I. (1982) Interleukin 1: A potential regulator of fibroblast proliferation. *Journal of Immunology* 128, 2177-2182.

Scorziello, T., Jandinski, J. J., Cai, H., Fenesy, K. & Deasy, M. J. (1990) Tumor necrosis factor alpha in crevicular fluid during periodontal health and disease. *Journal of Dental Research.* 68, (Special Issue), Abstract #1748.

Socransky, S. S. (1977) Microbiology of periodontal disease. Present status and future considerations. *Journal of Periodontology* 48, 497-504.

Stashenko, P., Dewhirst, F. E., Peros, W. J., Kent, R. L. & Ago, J. M. (1987) Synergistic interactions between interleukin 1, tumor necrosis factor, and lymphotoxin in bone resorption. *Journal of Immunology* 138, 1464-1468.

Stashenko, P., Dewhirst, F. E., Rooney, M. L., DesJardins, L. A. & Heeley, J. D. (1987) Interleukin 1β is a potent inhibitor of bone formation in vitro. *Journal of Bone and Mineral Research* 2, 559–565.

Tatakis, D. N., Schneeberger, G. & Dziak, R. (1988) Recombinant interleukin-1 stimulates prostaglandin E2 production by osteoblastic cells: synergy with parathyroid hormone. *Calcified Tissue International* 42, 358–362.

van Palenstein-Helderman, W. H. (1975) Total viable count and differential count of *Vibrio* (Campylobacter) *sputorum, Fusobacterium nucleatum, Selenomonas sputigena, Bacteroides ochraceus* and Veillonella in the inflamed and noninflamed human gingival crevice. *Journal of Periodontal Research* 10, 294–304.

I claim:

1. A method for the determination of periodontal disease active sites in the oral cavity of a patient, which method comprises:
   a) determining the concentration of interleukin 1 beta (IL-1b) of a sample taken from a site in the oral cavity; and
   (b) identifying the site as an active periodontal disease site when the concentration of interleukin 1 beta (IL-1b) is greater than about 25 ng/ml.

2. The method of claim 1 which includes correlating the concentration of the interleukin 1 beta (IL-1b) found at the site with healthy or diseased, but inactive, sites.

3. The method of claim 1 which includes determining the concentration of interleukin 1 beta (IL-1b) in gingival tissue taken from the site.

4. The method of claim 1 which includes determining the concentration of interleukin 1 beta (IL-1b) in gingival crevicular fluid (GCF) taken from said site.

5. The method of claim 1 which includes determining the concentration of interleukin 1 beta by an enzyme-linked immunoassay test.

6. The method of claim 1 which includes determining the concentration of interleukin 1 beta (IL-1b) in sites having a tissue loss of over about 2.5 mm within two months.

7. The method of claim 1 which includes determining the concentration of interleukin 1 beta (IL-1b) by an immunoassay test.

8. The method of claim 1 which includes obtaining a sample of gingival tissue or gingival crevicular fluid from a selected periodontal site in the oral cavity of a patient as the sample.

9. A method for the determination of periodontal disease active sites in the oral cavity of a patient, which method comprises:
   a) obtaining a sample of gingival tissue or gingival crevicular fluid from a selected periodontal site in the oral cavity of a patient;
   b) determining the concentration of interleukin 1 beta (IL-1b) of the sample; and
   c) identifying the site as an active periodontal disease site where the concentration of interleukin 1 beta (IL-1b) determined is greater than about 25 ng/ml.

* * * * *